US00PP14602P29

(12) United States Plant Patent
Verwer

(10) Patent No.: US PP14,602 P2
(45) Date of Patent: Mar. 16, 2004

(54) DAHLIA PLANT NAMED 'KARMA VENTURA'

(50) Latin Name: *Dahlia hybrida*
Varietal Denomination: Karma Ventura

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 10/437,955

(22) Filed: May 13, 2003

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—C. A. Whealy

(57) ABSTRACT

A distinct cultivar of Dahlia plant named 'Karma Ventura', characterized by its straight and strong flowering stems; freely basal branching growth habit; decorative-type inflorescence form; yellows-colored ray florets; excellent garden performance; and excellent inflorescence longevity.

2 Drawing Sheets

Botanical classification/cultivar designation: *Dahlia hybrida* cultivar Karma Ventura.

BACKGROUND OF THE INVENTION

The present Invention relates to a new and distinct cultivar of Dahlia plant, botanically known as *Dahlia hybrida* and hereinafter referred to by the name 'Karma Ventura'.

The new Dahlia is a product of a planned breeding program conducted by the Inventor in Lisse, The Netherlands. The objective of the breeding program is to create new cut flower Dahlia cultivars with straight strong flowering stems, decorative inflorescence form, attractive ray floret colors, and good inflorescence longevity.

The new Dahlia originated from a cross-pollination made by the Inventor during the summer of 1996 of two unidentified selections of *Dahlia hybrida,* not patented. The new Dahlia was discovered and selected by the Inventor as a single flowering plant within the progeny of the stated cross-pollination grown in a controlled environment in Lisse, The Netherlands, in August, 1997. The selection of this plant was based on its strong straight stems and attractive ray floret coloration.

Asexual reproduction of the new Dahlia by cuttings was first conducted in a controlled environment in Lisse, The Netherlands in the Spring of 1998. Asexual reproduction by cuttings has shown that the unique features of this new Dahlia are stable and reproduced true to type in successive generations.

SUMMARY OF THE INVENTION

The cultivar Karma Ventura has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Karma Ventura'. These characteristics in combination distinguish 'Karma Ventura' as a new and distinct Dahlia cultivar:

1. Straight and strong flowering stems.
2. Freely basal branching growth habit.

3. Decorative-type inflorescence form.
4. Bright yellow-colored ray florets.
5. Excellent garden performance.
6. Excellent inflorescence longevity.

Plants of the new Dahlia differ primarily from plants of the parent selections in ray floret coloration.

Plants of the new Dahlia can be compared to plants of the cultivar Glory of Heemstede, not patented. In side-by-side comparisons conducted in Lisse, The Netherlands, plants of the new Dahlia differed from plants of the cultivar Glory of Heemstede in the following characteristics:

1. Plants of the new Dahlia were more freely branching than plants of the cultivar Glory of Heemstede.
2. Inflorescences of plants of the new Dahlia had more ray florets than inflorescences of plants of the cultivar Glory of Heemstede.
3. Ray floret coloration of plants of the new Dahlia was darker yellow than ray floret coloration of plants of the cultivar Glory of Heemstede.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph on the first sheet comprises a side perspective view of a typical flowering stem of 'Karma Ventura'.

The photograph on the second sheet is a close-up view of typical inflorescences of 'Karma Ventura'.

DETAILED BOTANICAL DESCRIPTION

In the following description, color references are made to The Royal Horticultural Society Colour Chart, 1995 Edition, except where general terms of ordinary dictionary significance are used. The aforementioned photographs and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three to four weeks after planting rooted cuttings. Plants were about three to four months old when the photographs and the description were taken.

Botanical classification: *Dahlia hybrida* cultivar Karma Ventura.

Parentage: Cross-pollination of two unidentified selections of *Dahlia hybrida,* not patented.

Propagation:

*Type.*—By vegetative cuttings.

*Time to initiate roots.*—Summer: About 10 days at 18° C. Winter: About 12 days at 18° C.

*Time to produce a rooted young plant.*—Summer: About 24 days at 18° C. Winter: About 27 days at 18 to 20° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type inflorescence cut Dahlia. Straight and strong flowering stems; inverted triangle; moderately vigorous.

*Plant height.*—About 120 cm.

*Plant diameter.*—About 46 cm.

*Flowering stem description.*—Quantity of flowering stems per plant: Pinched plants will produce about 10 to 12 flowering stems. Length: About 76 cm. Diameter: About 7 mm. Internode length: About 12 to 23 cm. Strength: Strong. Aspect: Erect, straight. Texture: Glabrous, smooth. Color: Towards base, 146C; towards apex, 146D.

*Foliage description.*—Arrangement: Leaves opposite; leaves may be simple or compound with three or five leaflets. Shape: Ovate. Apex: Acuminate. Base: Attenuate. Margin: Serrate, occasionally parted. Length: Simple leaves: About 14 cm. Compound leaves with three leaflets: About 20 cm. Compound leaves with five leaflets: About 24 cm. Width: Single leaves: About 6.4 cm. Compound leaves with three leaflets: About 21 cm. Compound leaves with five leaflets: About 23 cm. Venation pattern: Pinnate. Texture: Smooth, glabrous. Color: Developing foliage, upper surface: 137A. Developing foliage, lower surface: 191A or more green than 191A. Fully developed foliage, upper surface: 137A to darker than 137A. Fully developed foliage, lower surface: 191A. Venation, upper surface: 147B. Venation, lower surface: 146C. Petioles: Length: About 4.5 cm. Diameter: About 3 mm. Texture, upper and lower surfaces: Smooth, glabrous. Color, upper surface: 146D. Color, lower surface: 146C.

Inflorescence description:

*Appearance.*—Decorative-type inflorescence form. Inflorescences borne on terminals, arising from leaf axils. Ray and disc florets develop acropetally on the receptacle. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 22 days in an outdoor environment. As cut flowers, inflorescences maintain good color and substance for about 8 to 12 days in an indoor environment.

*Quantity of inflorescences per flowering stem.*—One per lateral stem; about seven inflorescences per flowering stem; about 70 inflorescences per plant develop during the growing season.

*Inflorescence size.*—Shape, in profile: Roughly hemispherical. Diameter: About 13 cm. Depth (height): About 8.5 cm. Diameter of disc: About 3.8 cm; inconspicuous. Receptacle diameter: About 1.2 cm. Receptacle height: About 1.5 mm.

*Inflorescence buds* (*just before opening*).—Length: About 1.4 cm. Diameter: About 2.1 cm. Shape: Oblate. Color: 151A.

*Ray florets.*—Length, fully developed: About 6.2 cm. Width, fully developed: About 2.1 cm. Shape: Elongated oblong. Apex: Acute. Base: Attenuate. Margin: Entire. Texture: Smooth, glabrous; shiny. Number of ray florets per inflorescence: About 176 arranged in about 22 rows. Venation pattern: Parallel. Color: When opening, upper surface: 1A. When opening, lower surface: 1C. Fully opened, upper surface: 1A. Fully opened, lower surface: 1B.

*Disc florets.*—Number of disc florets per inflorescence: About 14. Shape: Tubular, elongated. Apex: Five-pointed. Base: Attenuate. Length: About 1.6 cm. Diameter, apex: About 2 mm. Diameter, base: About 3 mm. Color: Immature: 2C. Mature: Apex: 14A. Mid-section: 14B. Base: 1B.

*Phyllaries.*—Quantity: One whorl with about 8 phyllaries. Shape: Ovate. Apex: Acute. Base: Attenuate. Margin: Entire. Length: About 2.4 cm. Width: About 1 cm. Texture, upper and lower surfaces: Smooth, glabrous. Color, upper surface: 138A. Color, lower surface: 138B.

*Peduncles.*—Length, terminal peduncle: About 70 cm. Length, fourth peduncle: About 28 cm. Length, seventh peduncle: About 18 cm. Diameter: About 3 mm. Strength: Strong. Texture: Smooth, glabrous. Color: 151B.

*Reproductive organs.*—Androecium: Present on disc florets only. Stamen quantity: About five per floret. Anther length: About 4 mm. Anther color: 21B. Pollen amount: Scarce. Pollen color: 17A. Gynoecium: Present on ray and disc florets. Pistil quantity: One per floret. Pistil length: About 3 mm. Stigma color: 25B. Style length: About 2 mm. Style color: 150C. Ovary color: 2D.

*Seeds/fruits.*—Seed and fruit development has not been observed.

Disease/pest resistance: Resistance to pathogens and pests common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Karma Ventura', as illustrated and described.

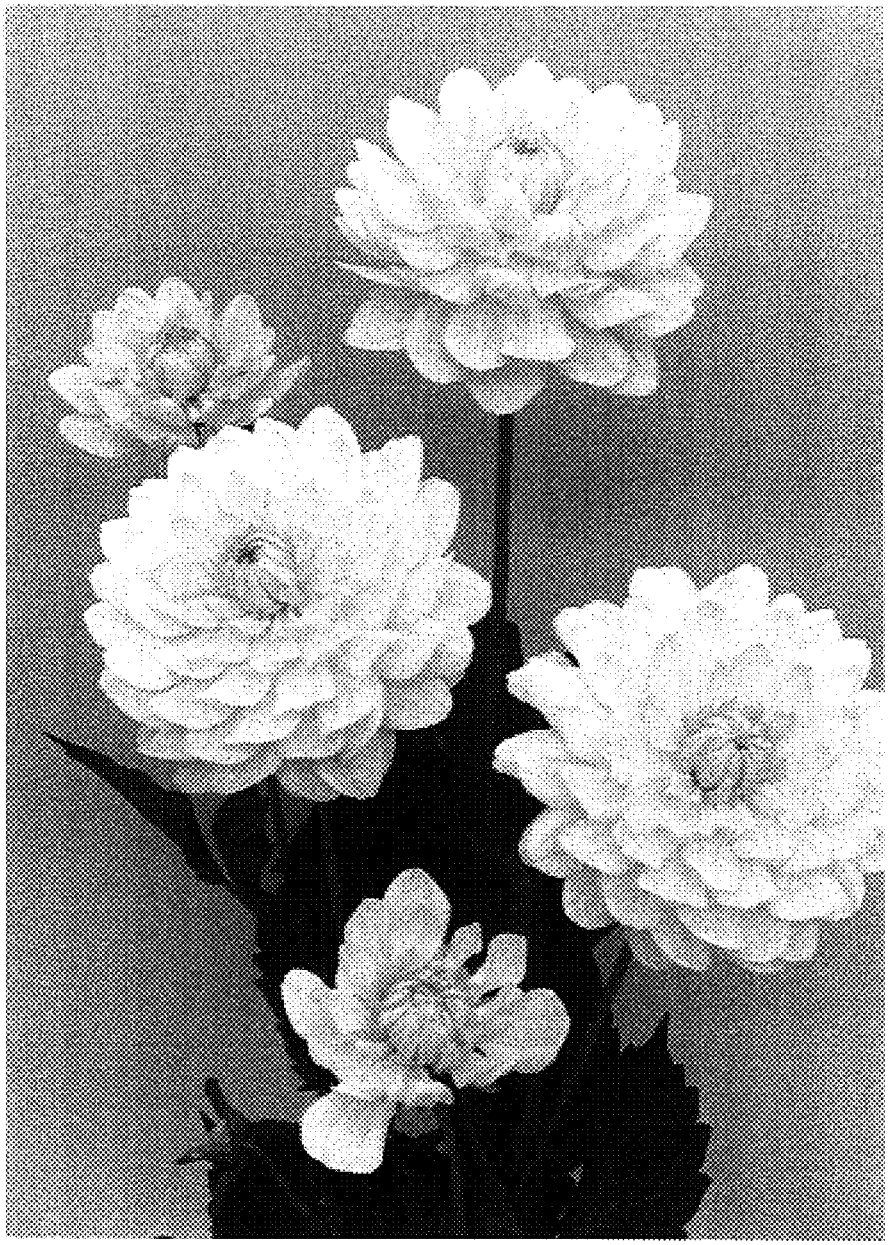

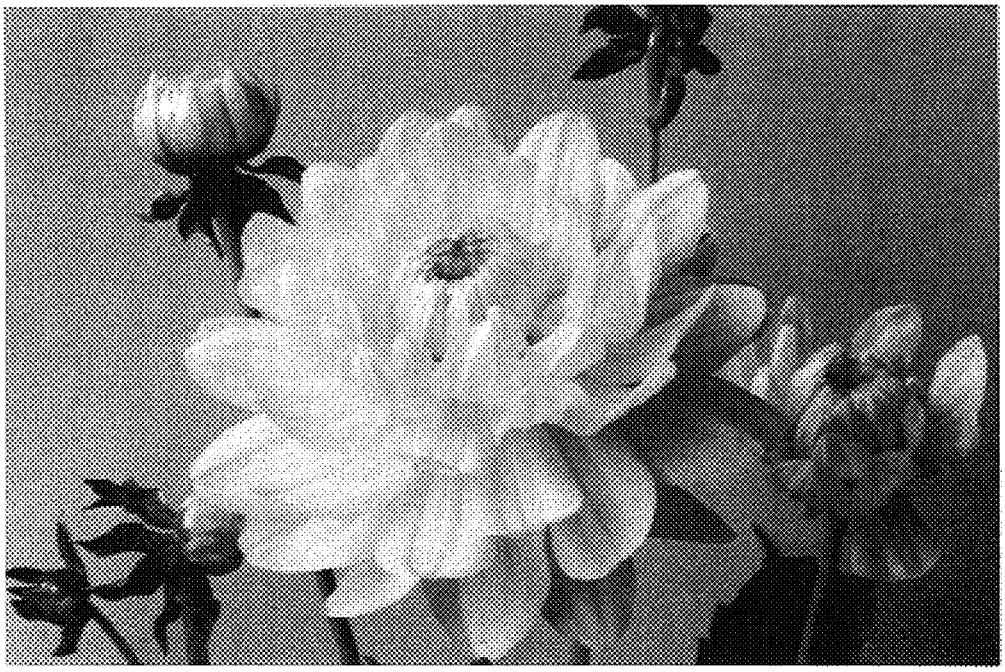

* * * * *